(12) United States Patent
Shibata et al.

(10) Patent No.: US 9,107,631 B2
(45) Date of Patent: Aug. 18, 2015

(54) ULTRASONIC IMAGING APPARATUS AND A METHOD FOR GENERATING AN ULTRASONIC IMAGE

(75) Inventors: Chihiro Shibata, Nasushiobara (JP); Muneki Kataguchi, Nasushiobara (JP); Atsushi Sumi, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1130 days.

(21) Appl. No.: 12/205,134

(22) Filed: Sep. 5, 2008

(65) Prior Publication Data

US 2009/0069684 A1 Mar. 12, 2009

(30) Foreign Application Priority Data

Sep. 7, 2007 (JP) ................................ 2007-233082

(51) Int. Cl.
*A61B 8/14* (2006.01)
*A61B 8/00* (2006.01)
*A61B 8/08* (2006.01)

(52) U.S. Cl.
CPC ............. *A61B 8/4281* (2013.01); *A61B 8/0833* (2013.01); *A61B 8/14* (2013.01)

(58) Field of Classification Search
USPC .......................................... 600/407, 437–475
See application file for complete search history.

(56) References Cited

U.S. PATENT DOCUMENTS

| | | | |
|---|---|---|---|
| 6,248,070 B1 * | 6/2001 | Kanda et al. ................... | 600/443 |
| 2005/0187463 A1 * | 8/2005 | Quistgaard et al. ........... | 600/424 |
| 2005/0256402 A1 * | 11/2005 | Kawashima et al. .......... | 600/437 |
| 2006/0058651 A1 * | 3/2006 | Chiao et al. .................... | 600/437 |
| 2007/0167709 A1 * | 7/2007 | Slayton et al. ................. | 600/407 |
| 2007/0167760 A1 * | 7/2007 | Kim et al. ...................... | 600/437 |

FOREIGN PATENT DOCUMENTS

JP 2006-51360 2/2006

* cited by examiner

*Primary Examiner* — Mark Remaly
(74) *Attorney, Agent, or Firm* — Oblon, McClelland, Maier & Neustadt, L.L.P.

(57) ABSTRACT

An imaging part transmits ultrasonic waves to a subject and receives reflected waves from the subject, thereby acquiring plural volume data of the subject. A specifying part specifies a surface site included in a face corresponding to the surface of the subject, in each of the plural volume data. A synthesizer executes position matching of the subject shown in each of the plural volume data. The synthesizer couples the plural volume data after position matching, and couples the respective surface sites specified in the respective volume data, thereby generating synthesized volume data. Based on the synthesized volume data, an image generator generates morphology image data showing the morphology of the subject and surface image data showing the coupled surface sites. A display controller controls a display to display a morphology image based on the morphology image data and a surface image based on the surface image data.

21 Claims, 10 Drawing Sheets

ULTRASONIC IMAGING APPARATUS AND A METHOD FOR GENERATING AN ULTRASONIC IMAGE

BACKGROUND OF THE INVENTION

1. Field of the Invention

The present invention relates to an ultrasonic imaging apparatus configured to scan a subject with ultrasonic waves to generate an image showing the morphology of the subject and an image showing the surface of the subject, and also relates to a method for generating an ultrasonic image.

2. Description of the Conventional Techniques

An ultrasonic imaging apparatus is capable of 3-dimensionally scanning a subject with ultrasonic waves to acquire volume data of the subject (e.g., Japanese Unexamined Patent Application Publication JP-A 2006-51360). In conventional techniques, by scanning while changing the position of an ultrasonic probe on the surface of a subject's body and coupling volume data acquired at the respective positions, volume data of a wider range is generated.

However, in the conventional techniques, even when coupling a plurality of volume data, it is difficult to grasp which site of the subject has been scanned, from the volume data. For example, in the mammary gland region, the internal structure is very similar at each site. Therefore, when reexamining the mammary gland region, it is difficult to grasp which site in the mammary gland region has been scanned, from a 3-dimensional image based on the volume data.

Further, in the acquired volume data, if a region of interest (ROI) is set to a site showing the inside of a subject's body, a region other than the ROI is eliminated and only an image of the ROI is displayed. Because the surface of the subject's body is not shown in the image, it is difficult to grasp the positional relationship between the surface of the subject's body and the ROI.

On the other hand, in the acquired volume data, if the site showing the surface of the subject's body is included in the ROI, an image showing the surface of the body is displayed. However, because the surface of the body is displayed as an image, the inside of the subject' body is not displayed in the image. Therefore, when executing an operation or puncture, it is not possible to previously display an image showing the internal structure of the subject, so that it is impossible to fully utilize information of the volume data.

As stated above, in the conventional techniques, it is difficult to grasp the positional relationship between the surface of a subject's body and a region of interest (ROI) when setting the region of interest (ROI) to a site showing the inside of the subject as well as when setting the region of interest (ROI) to the surface of the subject's body. Consequently, it is difficult to grasp which site of the subject has been scanned.

SUMMARY OF THE INVENTION

An object of the present invention is to provide an ultrasonic imaging apparatus capable of generating an image showing the positional relationship between a morphology image showing the morphology of a subject and the surface of the subject, and also relates to a method for generating an ultrasonic image.

In a first aspect of the present invention, an ultrasonic imaging apparatus comprises: an imaging part configured to transmit ultrasonic waves to a subject and receive reflected waves from the subject, thereby acquiring a plurality of volume data of the subject; a specifying part configured to specify a surface site included in a face corresponding to a surface of the subject, in each of the plurality of volume data; a synthesizer configured to execute position matching of the subject shown in each of the plurality of volume data, couple the plurality of volume data after position matching, and couple the surface sites specified in the respective volume data, thereby generating synthesized volume data; an image generator configured to generate morphology image data showing a morphology of the subject and surface image data showing the coupled surface sites based on the synthesized volume data; and a display controller configured to control a display to display a morphology image based on the morphology image data and a surface image based on the surface image data.

According to the first aspect, by specifying a surface site on the surface of a subject based on volume data and generating morphology image data showing the morphology of the subject and surface image data showing the surface site based on the volume data, it is possible to display a surface image showing the positional relationship between the morphology image and the surface of the subject. Consequently, an operator can easily grasp the relative positional relationship between the morphology image and the surface of the subject.

In a second aspect of the present invention, a method for generating an ultrasonic image comprises: transmitting ultrasonic waves to a subject and receiving reflected waves from the subject, thereby acquiring a plurality of volume data of the subject; specifying a surface site included in a face corresponding to a surface of the subject, in each of the plurality of volume data; executing position matching of the subject shown in each of the plurality of volume data, coupling the plurality of volume data after the position matching, and coupling the surface sites specified in the respective volume data, thereby generating synthesized volume data; generating morphology image data showing a morphology of the subject and surface image data showing the coupled surface sites based on the synthesized volume data; and displaying a morphology image based on the morphology image data and a surface image based on the surface image data.

DETAILED DESCRIPTION OF THE EMBODIMENTS

An ultrasonic imaging apparatus according to an embodiment of the present invention will be described with reference to FIG. 1.

Figure 1:
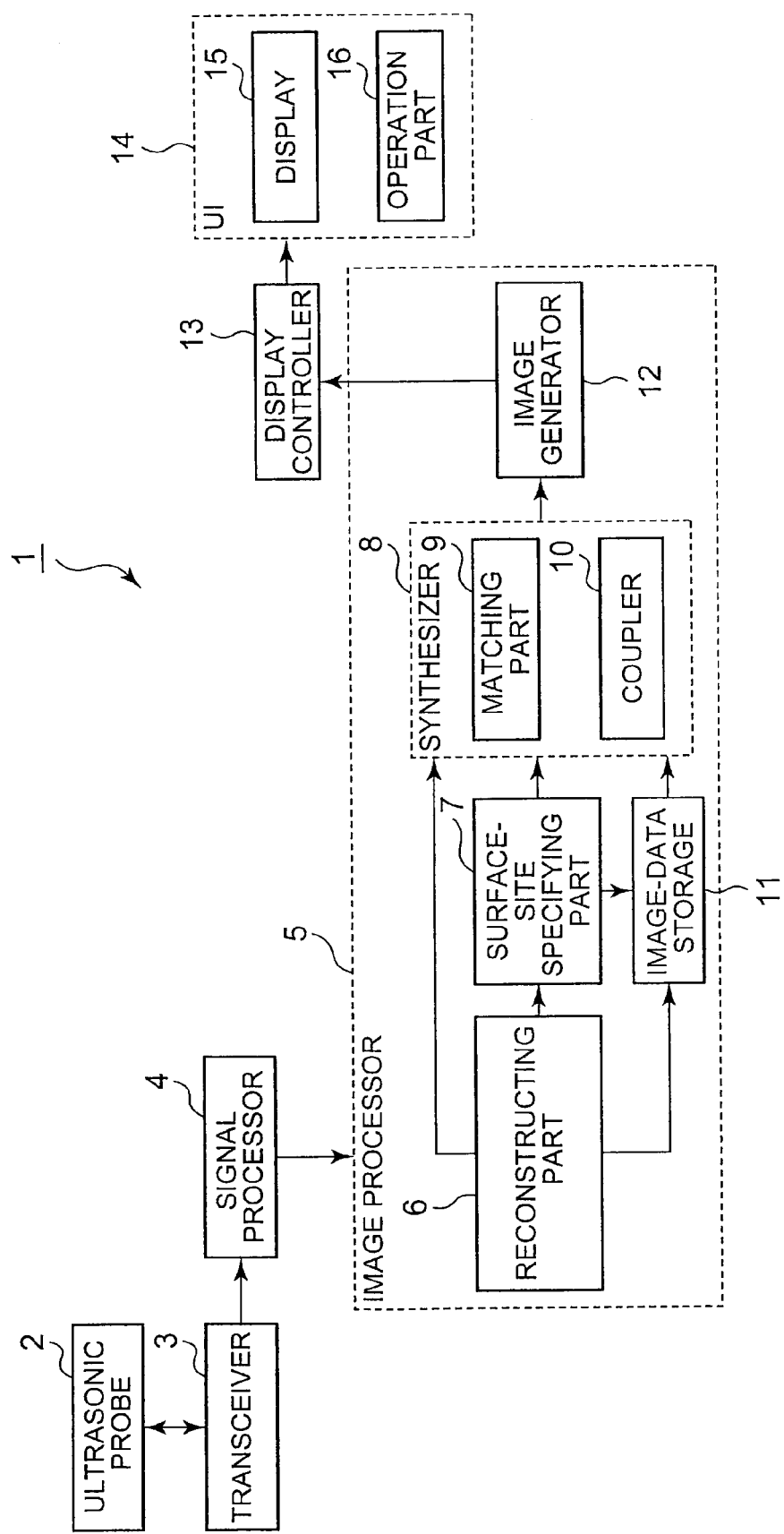
FIG. 1 is a block diagram showing an ultrasonic imaging apparatus according to an embodiment of the present invention.

FIG. 1 is a block diagram illustrating the ultrasonic imaging apparatus according to the embodiment of the present invention.

An ultrasonic imaging apparatus 1 according to this embodiment is provided with an ultrasonic probe 2, a transceiver 3, a signal processor 4, an image processor 5, a display controller 13 and a user interface (UI) 14. Moreover, an ultrasonic image processing apparatus is composed of the image processor 5, the display controller 13, and the user interface (UI) 14.

As the ultrasonic probe 2, a 1D array probe with a plurality of ultrasonic transducers aligned in a specified direction (a scanning direction), or a 2D array probe with a plurality of ultrasonic transducers arranged 2-dimensionally is used. The 2D array probe can scan a 3-dimensional region by transmission and reception of ultrasonic waves. Alternatively, as the ultrasonic probe 2, a mechanical-type 1D array probe with ultrasonic transducers aligned in the scanning direction that can scan a 3-dimensional region by oscillating the ultrasonic transducers in a direction orthogonal to the scanning direction (oscillating direction) may be used.

The transceiver 3 is provided with a transmitter and a receiver.

The transceiver 3 supplies electrical signals to the ultrasonic probe 2 so as to generate ultrasonic waves and receives echo signals received by the ultrasonic probe 2.

The transmitter of the transceiver 3 is provided with a clock generation circuit, a transmission delay circuit, and a pulsar circuit, which are not shown. The clock generation circuit generates a clock signal determining the transmission timing and transmission frequency of ultrasonic signals. The transmission delay circuit executes transmission focus by applying a delay at the time of transmission of ultrasonic waves. The pulsar circuit has the same number of pulsars as the number of individual channels corresponding to the respective ultrasonic transducers. The pulsar circuit generates a driving pulse in the transmission timing with a delay and supplies electrical signals to each of the ultrasonic transducers of the ultrasonic probe 2.

The receiver of the transceiver 3 is provided with a preamplifier circuit, an A/D conversion circuit, a reception delay circuit, and an adder circuit. The preamplifier circuit amplifies echo signals outputted from each of the ultrasonic transducers of the ultrasonic probe 2 in each reception channel. The A/D conversion circuit executes A/D conversion of the amplified echo signals. The reception delay circuit applies a delay time necessary for determining reception directionality to the echo signals after the A/D conversion.

The adder circuit adds the delayed echo signals. By the addition, a reflection component from a direction according to the reception directionality is emphasized. The signals after the adding process by the transceiver 3 may be referred to as "RF data." The transceiver 3 outputs the RF data to the signal processor 4.

The signal processor 4 is provided with a B-mode processor.

The B-mode processor images amplitude information of the echo and generates B-mode ultrasonic raster data from the echo signals. More specifically, the B-mode processor executes band-pass filtering on the signals sent from the transceiver 3 and then detects the envelope curve of the output signals. Then, the B-mode processor images the amplitude information of the echo by executing a compression process by logarithmic transformation on the detected data.

Moreover, the signal processor 4 may be provided with a Doppler processor. The Doppler processor generates blood-flow information by the pulse wave Doppler method (PW Doppler method) or the continuous wave Doppler method (CW Doppler method). For example, the Doppler processor executes quadrature detection of the received signals sent from the transceiver 3 to extract a Doppler shift frequency component, and further executes the FFT (Fast Fourier Transform) process to generate the Doppler frequency distribution showing the blood-flow velocity.

The signal processor 4 may be provided with a CFM processor.

The CFM processor images moving blood-flow information. Blood-flow information includes information such as the velocity, dispersion and power, and is obtained as binary information.

The signal processor 4 outputs ultrasonic raster data to the image generator 5. For example, by scanning a 3-dimensional region with ultrasonic waves along a plurality of cross-sections by using the ultrasonic probe 2 and the transceiver 3, the received signals in each cross-section are generated. The signal processor 4 generates ultrasonic raster data in each cross-section based on the received signals in each cross-section and outputs the ultrasonic raster data in each cross-section to the image generator 5.

In this embodiment, scan (volume scan) of a 3-dimensional region in a subject's body is executed by the ultrasonic probe 2 and the transceiver 3. Through this volume scan, volume data showing the 3-dimensional region is acquired. The signal processor 4 outputs the volume data showing the 3-dimensional region to the image generator 5.

The ultrasonic probe 2, the transceiver 3, and the signal processor 4 comprise an example of the "imaging part" according to the present invention.

(Image Processor 5)

The image processor 5 is provided with a reconstructing part 6, a surface-site specifying part 7, a synthesizer 8, an image-data storage 11, and an image generator 12. Moreover, the synthesizer 8 is provided with a matching part 9 and a coupler 10.

(Reconstructing Part 6)

The reconstructing part 6 acquires ultrasonic raster data in a plurality of cross-sections from the signal processor 4. The reconstructing part 6 reconstructs volume data showing a 3-dimensional region based on the ultrasonic raster data in the plurality of cross-sections.

(Surface-Site Specifying Part 7)

The surface-site specifying part 7 specifies a face corresponding to the surface of the subject's body in the volume data generated by the reconstructing part 6. In addition, the surface-site specifying part 7 specifies a surface site included in the specified face. Alternatively, the surface-site specifying part 7 may receive the volume data from the signal processor 4 and specify a surface site on the subject in the volume data. A method for generating the volume data is not particularly limited and it may be generated or acquired by any method. Furthermore, the surface-site specifying part 7 is specified to an example of the "specifying part" according to the present invention.

Figure 2:
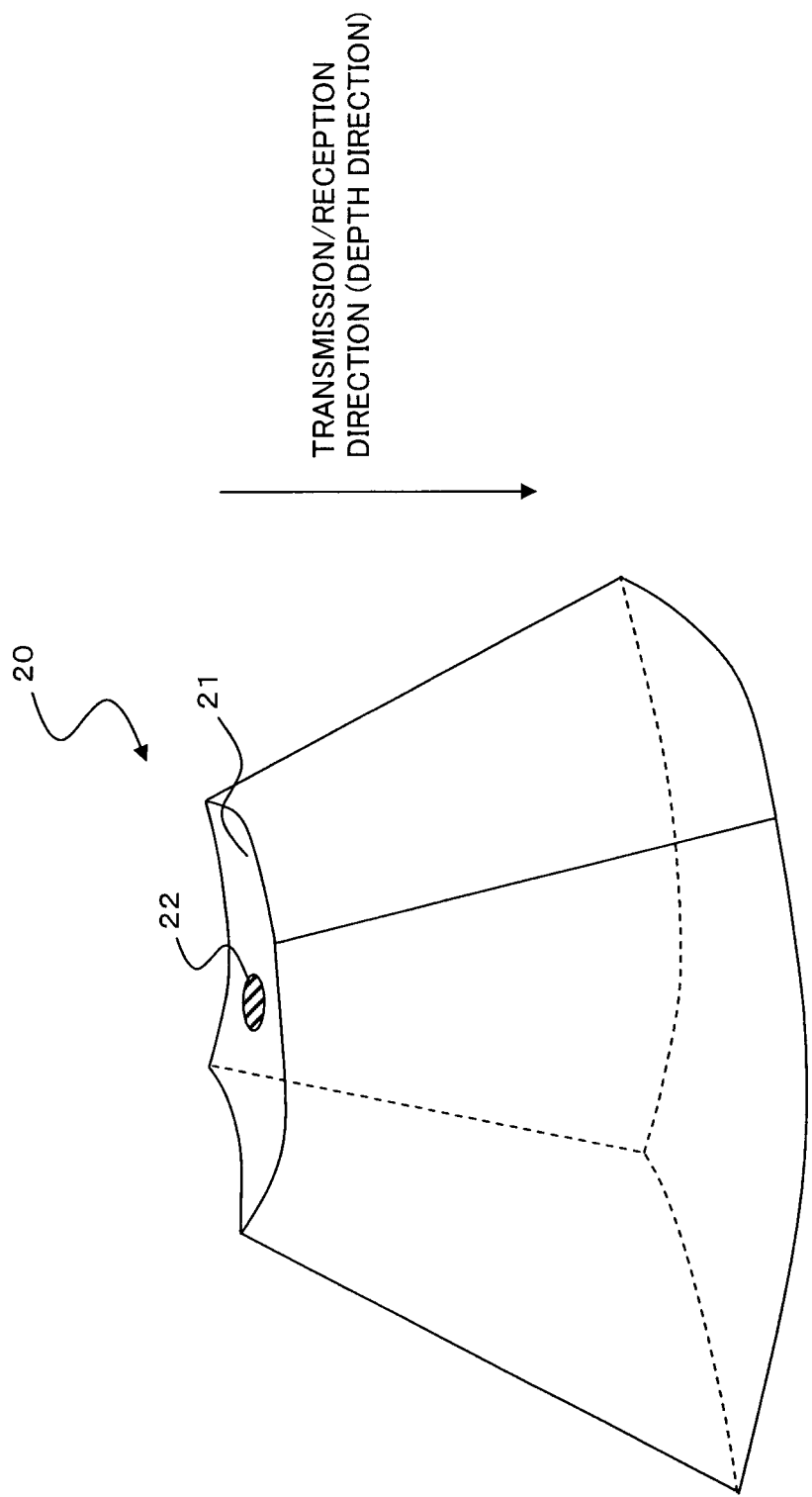
FIG. 2 is a schematic view for describing a surface site in volume data.

Here, a method for specifying a surface site will be described with reference to FIG. 2. FIG. 2 is a schematic view for describing a surface site in the volume data. Volume data 20 is defined by a 3-dimensional coordinate system. The surface-site specifying part 7 specifies a face 21 that is at the shallowest position in depth in a transmission/reception direction (depth direction) of ultrasonic waves and is substantially orthogonal to the transmission/reception direction. Then, the surface-site specifying part 7 defines the face 21 as a face corresponding to the surface of the subject. In this embodiment, a direction in which an ultrasonic beam is formed by transmission and reception by the ultrasonic probe 2 is defined as the transmission/reception direction (depth direction) of the ultrasonic waves. At the time of scan of the subject with ultrasonic waves, the volume data 20 is acquired by bringing a face for transmitting and receiving ultrasonic waves of the ultrasonic probe 2 in contact with the surface of the subject's body and scanning a 3-dimensional region in this state. Therefore, the face 21 that is at the shallowest position in depth (the position of 0 cm in depth) in the volume data 20 corresponds to the transmission/reception face of the ultrasonic probe 2. That is, the face 21 corresponds to the surface of the subject.

Then, the surface-site specifying part 7 specifies a surface site of the subject within the face 21. For example, the surface-site specifying part 7 obtains a center position of the face 21. Then, the surface-site specifying part 7 specifies a surface site 22 including the center position and having a specified width. Alternatively, the surface-site specifying part 7 may obtain a position with the strongest reflected waves of ultrasonic waves (a position with the highest pixel value) within the face 21 and specify a site including the position and having a specified width as the surface site 22.

Alternatively, the surface-site specifying part 7 may specify the entire face 21 as the surface site of the subject.

Figure 3:
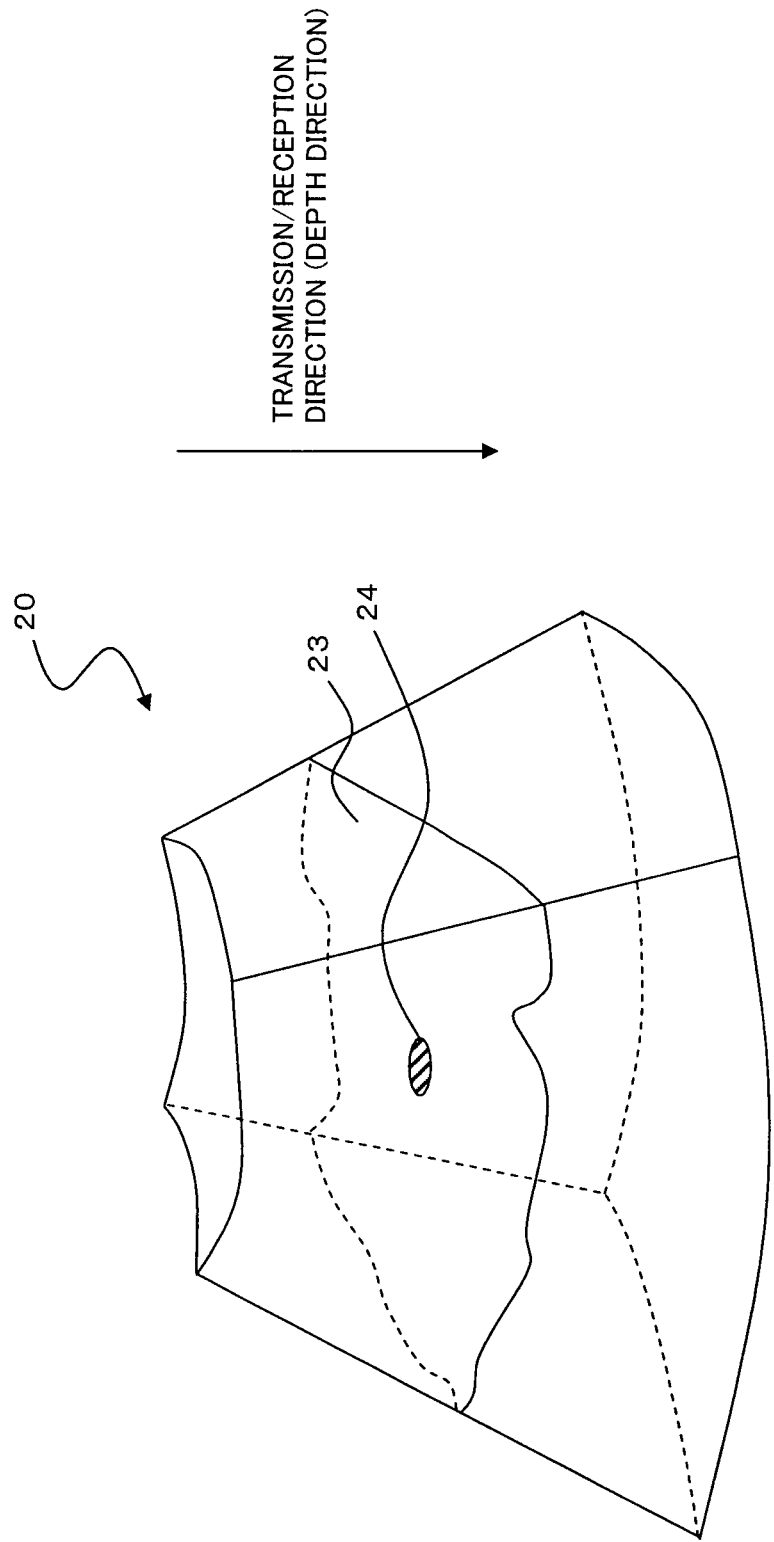
FIG. 3 is a schematic view for describing a surface site in volume data.

Another method for specifying a surface site will be described with reference to FIG. 3. FIG. 3 is a schematic view for describing a surface site in the volume data. In this example, the surface-site specifying part 7 specifies a place 24 where the strength of reflected waves of ultrasonic waves (the magnitude of the pixel value) is a specified value or more along the transmission/reception direction of the ultrasonic waves (the depth direction) in the volume data 20.

Then, the surface-site specifying part 7 specifies a face 23 including the specified place and substantially orthogonal to the transmission/reception direction. The surface-site specifying part 7 defines the face 23 as a face corresponding to the surface of the subject. That is, the surface-site specifying part 7 specifies the place 24 where the strength of the reflected waves (the magnitude of the pixel value) first becomes a specified value in the transmission/reception direction (the depth direction) in the volume data 20. The surface-site specifying part 7 then defines the face 23 including the place 24 as a face corresponding to the surface of the subject.

For example, in diagnosis of mammary glands, a method called the immersion method is employed. In this immersion method, a medium such as water is provided between the ultrasonic probe 2 and a subject (breast), and the subject is scanned with ultrasonic waves via the medium. Since the transmission/reception face of the ultrasonic probe 2 does not contact the surface of the subject's body, the face at the shallowest position in depth (the position of 0 cm in depth) in the volume data 20 does not correspond to the surface of the subject. Therefore, in the example shown in FIG. 3, the face 23 that includes the place 24 where the strength of the reflected waves (the magnitude of the pixel value) first becomes a specified value in the depth direction is defined as the face corresponding to the surface of the subject.

To be specific, a threshold for the strength of the reflected waves from the surface of the subject is preset in the surface-site specifying part 7. The surface-site specifying part 7 specifies a place where the strength of the reflected waves (the magnitude of the pixel value) first becomes the threshold in the depth direction in the volume data 20. The surface-site specifying part 7 then defines a face including the place as the surface of the subject.

Then, the surface-site specifying part 7 specifies a surface site of the subject within the face 23. For example, the surface-site specifying part 7 obtains the center position of the face 23. The surface-site specifying part 7 then determines a site that includes the center position and has a specified width as a surface site of the subject. Alternatively, the surface-site specifying part 7 may determine the place 24 where the strength of the reflected waves (magnitude of the pixel value) becomes the threshold or more, as the surface site. Alternatively, the surface-site specifying part 7 may determine the entire face 23 as the surface site.

The reconstructing part 6 outputs the volume data to the image-data storage 11. The image-data storage 11 stores the volume data outputted from the reconstructing part 6. Moreover, when the surface site is specified as shown in FIG. 2 and FIG. 3, the surface-site specifying part 7 outputs coordinate information showing the position of the specified surface site to the image-data storage 11.

The image-data storage 11 stores the coordinate information of the surface site and the volume data in a state where the coordinate information of the surface site is incidental to the volume data.

In this embodiment, the ultrasonic probe 2 is brought into contact with the surface of the subject, and the ultrasonic probe 2 is moved on the surface of the subject while scan with ultrasonic waves is executed. Thus, by scanning while changing the position of the ultrasonic probe 2 on the surface of the subject, volume data is acquired at respective positions. Consequently, a plurality of volume data is acquired at various sites of the subject.

When volume data is newly generated, the surface-site specifying part 7 specifies a surface site for the new volume data.

The reconstructing part 6 then outputs the new volume data to the synthesizer 8. Moreover, the surface-site specifying part 7 outputs coordinate information of the surface site in the new volume data to the synthesizer 8.

(Synthesizer 8)

The synthesizer 8 reads out the volume data from the image-data storage 11, and couples the read-out volume data and the new volume data, thereby generating synthesized volume data. The synthesizer 8 then outputs the synthesized volume data to the image-data storage 11. The image-data storage 11 stores the newly generated synthesized volume data, in place of the previously stored volume data. That is, the image-data storage 11 updates the data and stores newly generated synthesized volume data.

Figure 4:
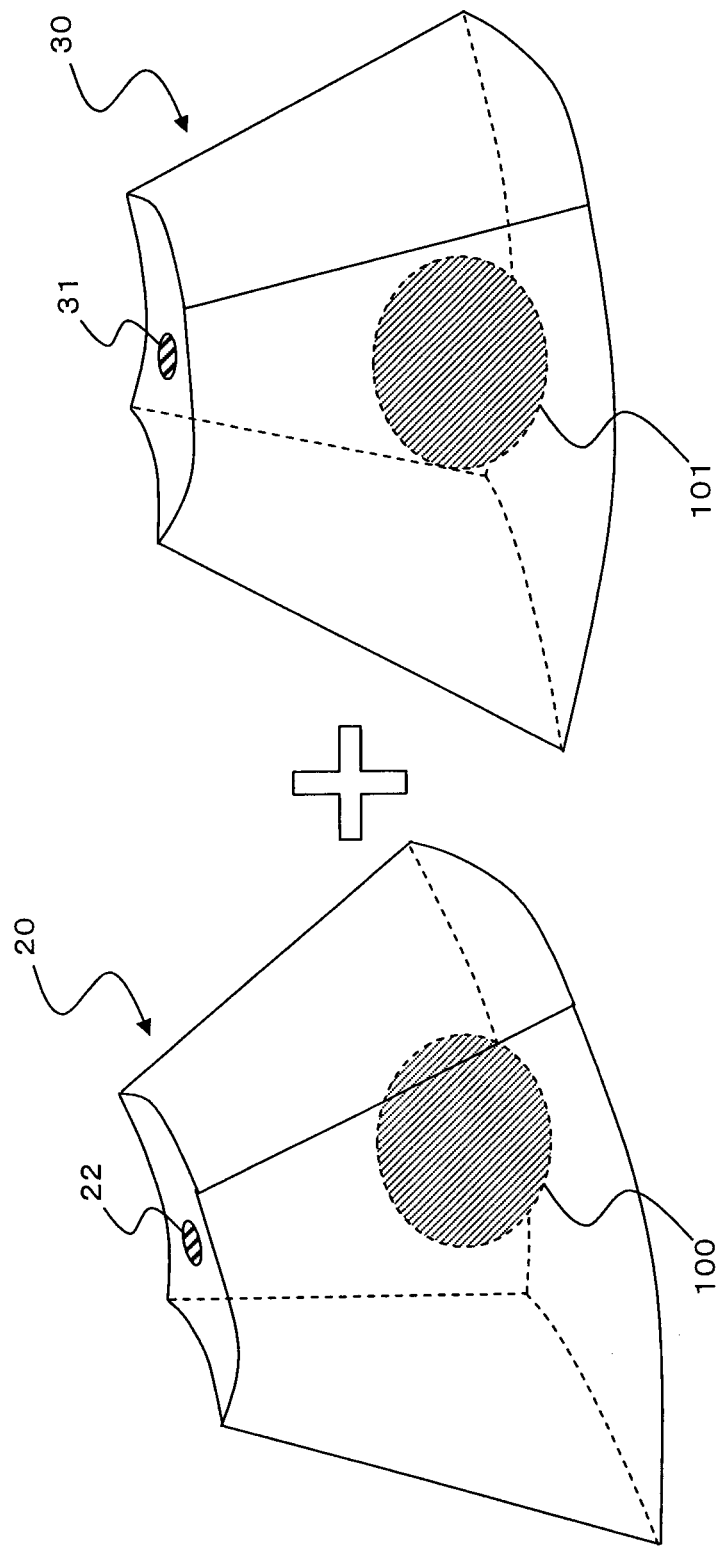
FIG. 4 is a schematic view for describing a process of synthesizing volume data.
Figure 5:
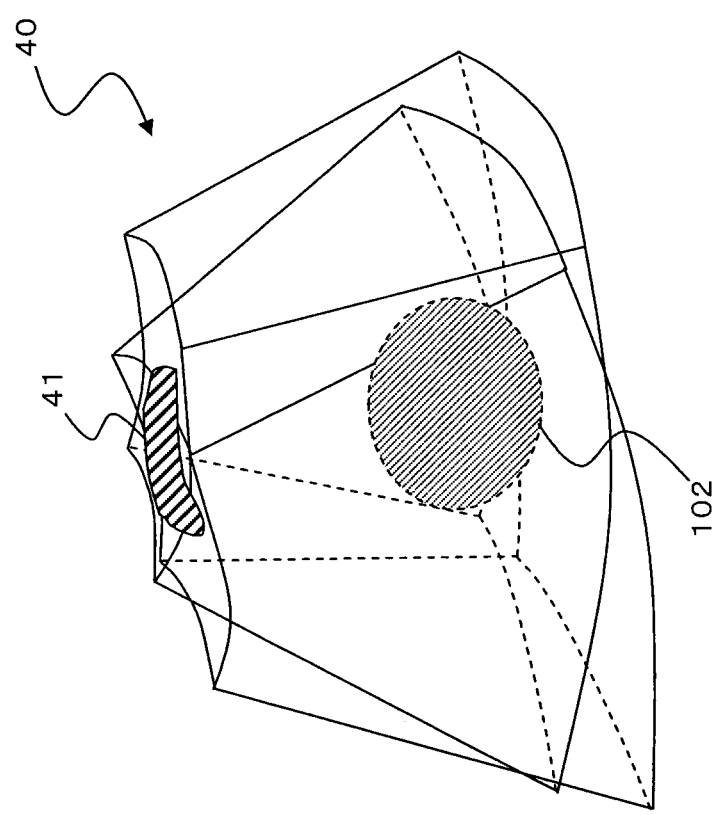
FIG. 5 is a schematic view for describing a process of synthesizing volume data.

Here, the details of processing by the synthesizer 8 will be described with reference to FIG. 4 and FIG. 5. FIG. 4 and FIG. 5 are schematic views for describing a process of synthesizing the volume data. FIG. 4 shows two volume data before coupling. FIG. 5 shows synthesized volume data after the coupling.

As an example, as shown in FIG. 4, coupling of the previously generated volume data 20 and newly generated volume data 30 will be described. In the image-data storage 11, the previously generated volume data 20 and the coordinate information of the surface site 22 are stored. When the new volume data 30 is generated, the surface-site specifying part 7 specifies a surface site 31 for the new volume data 30. In the example shown in FIG. 4, a face at the shallowest position in depth in the transmission/reception direction of the ultrasonic waves (the depth direction) is determined as a face corresponding to the surface of the subject. Additionally, a place including the center position of the face and having a specified width is determined as the surface site.

The reconstructing part 6 outputs the newly generated volume data 30 to the synthesizer 8. Moreover, the surface-site specifying part 7 outputs coordinate information of the surface site 31 in the new volume data 30, to the synthesizer 8.

(Matching Part 9)

The matching part 9 of the synthesizer 8 matches the positions on the subject shown in the two volume data, by executing pattern matching on the morphology of the subject shown in the two volume data. For example, the matching part 9 reads out the volume data 20 stored in the image-data storage 11, and further receives the volume data 30 from the reconstructing part 6, thereby matching positions on the subjects shown in the volume data 20 and the volume data 30. In the example shown in FIG. 4, the matching part 9 matches the positions of the subject shown in the volume data 20 and the volume data 30, by matching the morphology of an imaging site 100 shown in the volume data 20 with the morphology of an imaging site 101 shown in the volume data 30. The volume data 20 and the volume data 30 are data acquired at different positions on the surface of the subject's body. Moreover, the imaging site 100 shown in the volume data 20 and the imaging site 101 shown in the volume data 30 are sites shown in the respective volume data by scanning the same imaging object with ultrasonic waves.

(Coupler 10)

The coupler 10 of the synthesizer 8 couples the two volume data whose positions have been matched by the matching part 9, and thereby generates one synthesized volume data. For example, as shown in FIG. 5, the coupler 10 couples the volume data 20 and the volume data 30, thereby generating synthesized volume data 40. An imaging site 102 is shown in the synthesized volume data 40.

The coupler 10 may obtain a mean of the volume data 20 and the volume data 30 in a part where the volume data 20 overlaps the volume data 30 and determine the mean as data of the overlapping part.

Moreover, the coupler 10 may generate data showing a new surface site by interpolating data between the surface site 22 and the surface site 23. For example, the coupler 10 generates data showing a new surface site 41 by executing an interpolation process such as linear interpolation and spline interpolation on data between the surface site 22 and the surface site 23.

Then, the synthesizer 8 outputs the newly generated synthesized volume data 40 and coordinate information of the surface site 41 to the image-data storage 11. The image-data storage 11 stores the coordinate information of the surface site 41 in the incidental state to the synthesized volume data 40. The image-data storage 11 stores the newly generated synthesized volume data 40, in place of the previously stored volume data. Moreover, the synthesizer 8 outputs the synthesized volume data 40 and the coordinate information of the surface site 41 to the image generator 12.

The ultrasonic probe 2 may be equipped with a position sensor so as to detect a position where each volume data has been acquired with the position sensor. For example, volume data at each position is acquired while the ultrasonic probe 2 is moved on the surface of the subject. Furthermore, the position sensor detects each position of the ultrasonic probe 2 on the subject. As the position sensor, a position sensor according to the conventional techniques may be used.

For example, by using a magnetic position sensor or an optical position sensor, the positions of the ultrasonic probe 2 on the subject are detected.

Coordinate information showing the position detected by the position sensor is outputted to the image processor 5. The image processor 5 attaches the coordinate information showing the position where the volume data has been acquired to each of volume data. The coupler 10 then couples the plurality of volume data based on the coordinate information of the respective volume data. In this case, the matching process by the matching part 9 is not performed, so the matching part 9 does not need to be provided. Furthermore, the position sensor corresponds to an example of the "position detector" according to the present invention.

The image generator 12 generates 3-dimensional image data that 3-dimensionally shows the morphology of the subject by executing volume rendering on the volume data. Moreover, the image generator 12 may generate image data (MPR image data) in an arbitrary cross-section by executing MPR process (Multi Plannar Reconstruction) on the volume data. The image generator 12 then outputs the ultrasonic image data such as 3-dimensional image data and MPR image data to the display controller 13.

For example, the image generator 12 sets a view direction for the synthesized volume data 40 and executes volume rendering on the synthesized volume data 40 along the view direction. Consequently, the image generator 12 generates 3-dimensional image data that 3-dimensionally shows the morphology of the imaging site 102 shown in the synthesized volume data 40, and surface image data showing a place (surface site 41) specified by the coordinate information of the surface site 41. The view direction can be designated to an arbitrary direction by the operator using an operation part 16. With the direction designated by the operator as the view direction, the image generator 12 executes volume rendering on the synthesized volume data along the view direction. The image generator 12 then outputs the 3-dimensional image data and surface image data to the display controller 13. Thus, the image generator 12 executes volume rendering on the synthesized volume data along the same view direction, thereby generating the 3-dimensional image data and the surface image data whose view directions coincide.

The display controller 13 receives the 3-dimensional image data and the surface image data from the image generator 12, and controls a display 15 to simultaneously display a 3-dimensional image based on the 3-dimensional image data and a surface image based on the surface image data. Consequently, the 3-dimensional image based on the synthesized volume data 40 and the surface image showing the surface site 41 are simultaneously displayed on the display 15. The 3-dimensional image data and the surface image data are generated along the same view direction, so the 3-dimensional image and the surface image can be viewed from the same direction.

That is, the direction of the 3-dimensional image coincides with the direction of the surface image.

Figure 6:
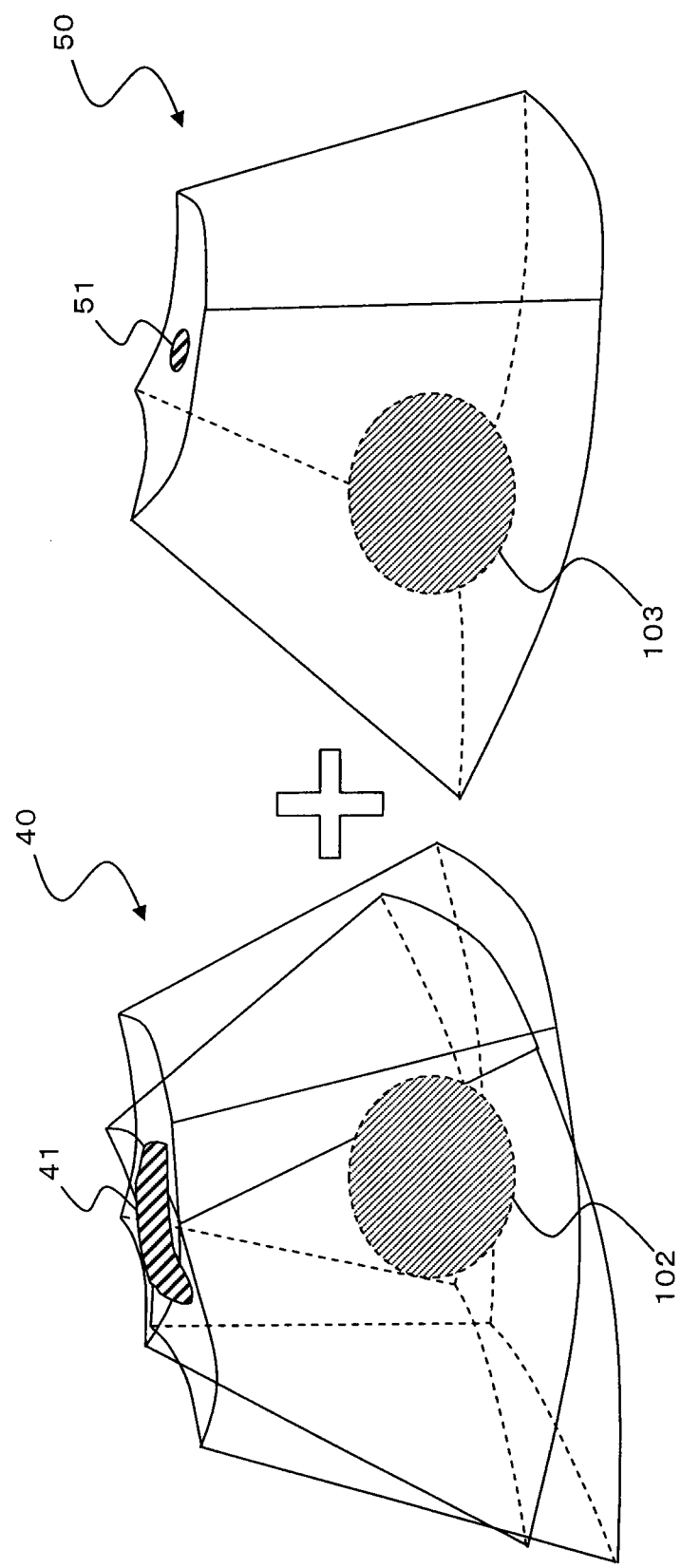
FIG. 6 is a schematic view for describing a process of synthesizing volume data.
Figure 7:
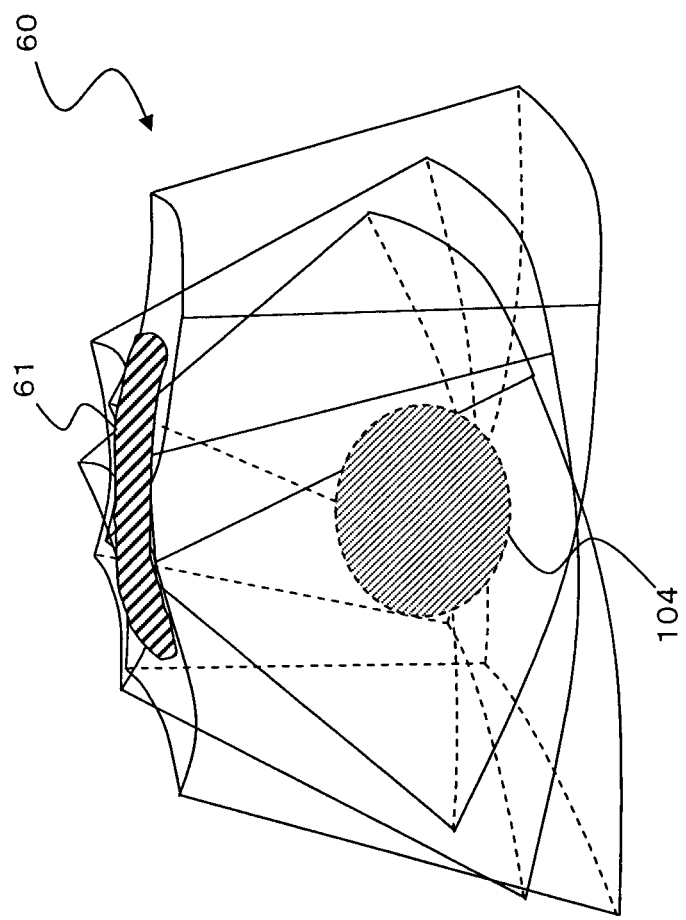
FIG. 7 is a schematic view for describing a process of synthesizing volume data.

When another new volume data is generated, the image processor 5 generates new synthesized volume data by repeating the abovementioned process. Generation of another new volume data will be described with reference to FIG. 6 and FIG. 7. FIG. 6 and FIG. 7 are schematic views for describing a process of synthesizing the volume data. FIG. 6 shows two volume data before coupling. FIG. 7 shows synthesized volume data after coupling.

The image-data storage 11 stores the previously generated synthesized volume data 40 and the coordinate information of the surface site 41. When new volume data 50 is generated, the surface-site specifying part 7 specifies a surface site 51 for the new volume data 50. The reconstructing part 6 outputs the newly generated volume data 50 to the synthesizer 8. Moreover, the surface-site specifying part 7 outputs coordinate information of the surface site 51 of the new volume data 50 to the synthesizer 8.

The matching part 9 reads out the synthesized volume data 40 stored in the image-data storage 11, further receives the volume data 50 from the reconstructing part 6, and matches the positions of the subject shown in the synthesized volume data 40 and the volume data 50. In the example shown in FIG. 6, the matching part 9 matches the positions of the subject shown in the synthesized volume data 40 and the volume data 50 by matching the morphology of the imaging site 102 shown in the synthesized volume data 40 with the morphology of an imaging site 103 shown in the volume data 50.

For example, as shown in FIG. 7, the coupler 10 couples the synthesized volume data 40 and the volume data 50 whose positions have been matched by the matching part 9, and thereby generates new synthesized volume data 60. An imaging site 104 is shown in the synthesized volume data 60. The coupler 10 executes an interpolation process such as linear interpolation and spline interpolation between the surface site 41 and a surface site 51, thereby generating data showing a new surface site 61.

Then, the synthesizer 8 outputs the newly generated synthesized volume data 60 and coordinate information of the surface site 61 to the image-data storage 11. The image-data storage 11 stores the coordinate information of the surface site 61 in the incidental state to the synthesized volume data 60. The image-data storage 11 stores the newly generated synthesized volume data 60, in place of the previously stored synthesized volume data 40. Moreover, the synthesizer 8 outputs the synthesized volume data 60 and the coordinate information of the surface site 61 to the image generator 12.

The image generator 12 sets a view direction for the synthesized volume data 60, and executes volume rendering on the synthesized volume data 60 along the view direction. Consequently, the image generator 12 generates 3-dimensional image data that 3-dimensionally shows the morphology of the imaging site 104 shown in the synthesized volume data 60, and the surface image data showing the surface site 61. Then, the image generator 12 outputs the 3-dimensional image data and the surface image data to the display controller 13. Thus, the image generator 12 executes volume rendering on the synthesized volume data along the same view direction, thereby generating the 3-dimensional image data and the surface image data whose view directions coincide.

The display controller 13 controls the display 15 to simultaneously display a 3-dimensional image based on the 3-dimensional image data and a surface image based on the surface image data. The display controller 13 controls the display 15 to display the newly generated 3-dimensional image and surface image, in place of the previously displayed 3-dimensional image and surface image. That is, every time new volume data is generated, the display controller 13 updates the 3-dimensional image and the surface image and controls the display 15 to display them. Consequently, the 3-dimensional image based on the synthesized volume data 60 and the surface image showing the surface site 61 are simultaneously displayed on the display 15. The 3-dimensional image data and the surface image data are generated along the same view direction, so the 3-dimensional image and the surface image can be viewed from the same direction.

Every time new volume data is generated by transmission and reception of ultrasonic waves, the image processor 5 generates new synthesized volume data, and specifies a surface site. The image generator 12 then generates 3-dimensional image data and surface image data based on the new synthesized volume data, and the display controller 13 updates the 3-dimensional image and the surface image and controls the display 15 to display them.

The image generator 12 may generate the 3-dimensional image data and the surface image data based on the volume data before the synthesizing process. For example, as shown in FIG. 2, the reconstructing part 6 generates the volume data 20 and outputs the volume data 20 to the image generator 12. Moreover, the surface-site specifying part 7 specifies the surface site 22 for the volume data 20 and outputs the coordinate information of the surface site 22 to the image generator 12. The image generator 12 sets a view direction for the volume data 20 and executes volume rendering on the volume data 20 along the view direction, thereby generating 3-dimensional image data that 3-dimensionally shows the imaging site 100 and the surface image data showing the surface site 22. Then, the display controller 13 controls the display 15 to simultaneously display the 3-dimensional image that 3-dimensionally shows the imaging site 100 and the surface image showing the surface site 22. In this manner, the 3-dimensional image and surface image before the synthesizing process may be displayed on the display 15.

Figure 8:
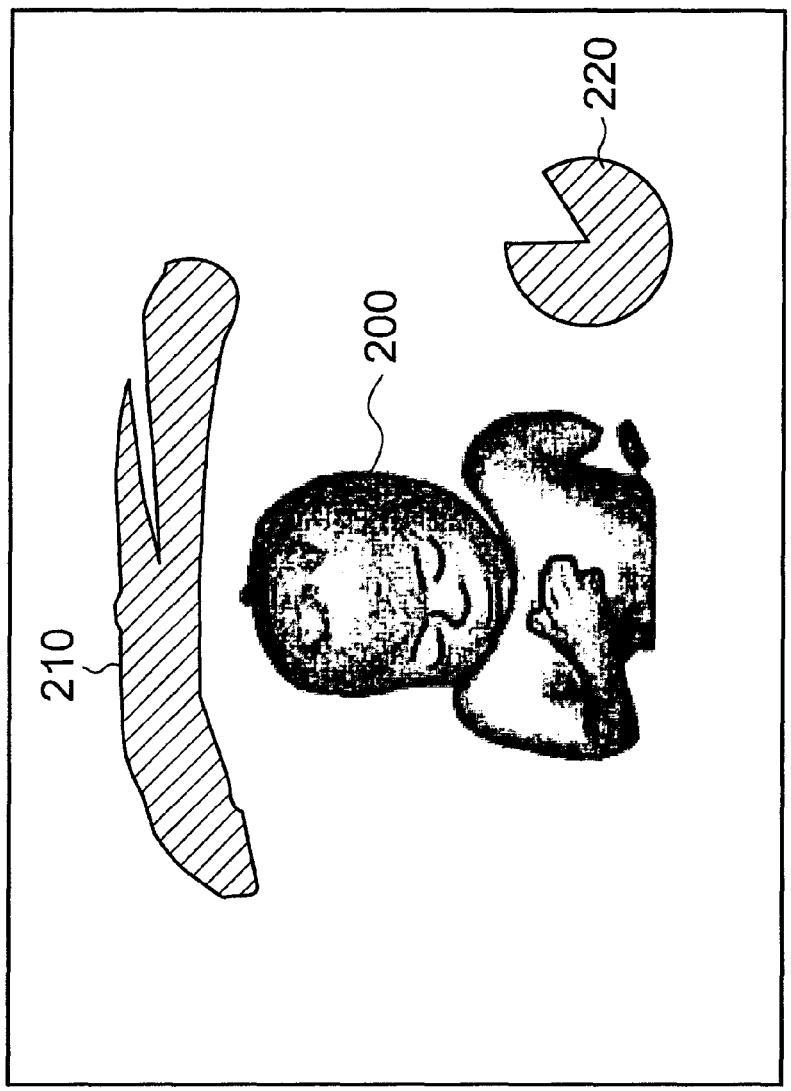
FIG. 8 is a view of a screen showing a 3-dimensional image and a surface image.

Here, an example of the 3-dimensional image and surface image displayed on the display 15 will be described with reference to FIG. 8. FIG. 8 is a view of a screen showing a 3-dimensional image and a surface image.

The display controller 13 controls the display 15 to simultaneously display a 3-dimensional image 200 showing an imaging site and a surface image 210 showing a surface site. The 3-dimensional image 200 3-dimensionally shows the imaging site. In this embodiment, the 3-dimensional image 200 3-dimensionally represents a fetus. Moreover, the surface image 210 represents the surface of a subject' body. Since the 3-dimensional image data and the surface image data are generated along the same view direction, the 3-dimensional image 200 and the surface image 210 are images viewed from the same direction. That is, the direction of the 3-dimensional image 200 coincides with the direction of the surface image 210. Therefore, the operator can grasp the relative positional relationship between the surface of the subject's body and the 3-dimensional image 200 by observing the 3-dimensional image 200 and the surface image 210. For example, it is possible to grasp the distance between the 3-dimensional image 200 and the surface of the subject's body.

As stated above, according to the ultrasonic imaging apparatus 1 of this embodiment, by specifying the surface site on the surface of the subject's body based on the volume data and simultaneously displaying the 3-dimensional image that 3-dimensionally shows the subject and the surface image showing the surface site of the subject's body, it is possible to easily grasp the relative positional relationship between the 3-dimensional image and the surface of the subject's body. Thus, the operator can easily grasp which site of the subject has been scanned. Consequently, it is possible to prevent examination omission, and more accurately grasp an examined site in reexamination.

(Region of Interest)

The image generator 12 may set a region of interest (ROI) for synthesized volume data and extract data included in the region of interest. Then, the image generator 12 generates 3-dimensional image data that 3-dimensionally shows the region of interest, based on the extracted data. Moreover, the image generator 12, as described above, generates surface image data showing a surface site, based on the synthesized volume data. Then, the display controller 12 controls the display 15 to display a 3-dimensional image showing the region of interest and a surface image showing the surface site.

The operator can designate the position of a region of interest (ROI) by using the operation part 16. For example, the display controller 13 controls the display 15 to display the 3-dimensional image, and the operator designates a desired region (a region of interest) on the 3-dimensional image by using the operation part 16.

Coordinate information indicating this designated region (region of interest) is outputted from the user interface (UI) 14 to the image generator 12. The image generator 12 extracts data included in the region of interest (ROI) from the synthesized volume data, in accordance with the coordinate information indicating the region of interest (ROI). Then, the image generator 12 generates 3-dimensional image data that 3-dimensionally shows the region of interest (ROI), based on the extracted data. The display controller 13 controls the display 15 to simultaneously display the 3-dimensional image of the region of interest (ROI) and the surface image showing the surface site.

Moreover, the image generator 12 may extract data showing a specific tissue based on a luminance difference in synthesized volume data. For example, the image generator 12 extracts data showing blood vessels based on the luminance difference, and generates 3-dimensional image data that 3-dimensionally shows the blood vessels based on the data. Then, the display controller 13 controls the display 15 to simultaneously display a 3-dimensional image of the blood vessels and a surface image showing the surface site. As the image extracting process, a method according to the conventional techniques may be employed.

As stated above, the operator can easily grasp the distance between the surface of the subject's body and the site included in the region of interest, etc., by controlling the display 15 to simultaneously display the 3-dimensional image showing the region of interest and the surface image showing the surface site. For example, when executing puncture, it is possible to grasp the distance between the surface of the subject's body and the blood vessel, by controlling the display 15 to display the 3-dimensional image showing the blood vessel and the surface image showing the surface site. Consequently, it is possible to execute puncture while avoiding the blood vessel.

(MPR Display)

Moreover, instead of generating 3-dimensional image data of the subject, the image generator 12 may generate image data (MPR image data) in an arbitrary cross-section by executing the MPR process on the synthesized volume data. Moreover, the image generator 12, as described above, generates the surface image data showing the surface site based on synthesized volume data. Then, the display controller 12 controls the display 15 to simultaneously display an MPR image based on the MPR image data and a surface image showing the surface site. Thus, an MPR image in an arbitrary cross-section is displayed on the display 15 regarding the morphology of the subject, and a surface image showing a specified surface site is displayed on the display 15 regarding the surface site.

An arbitrary cross-section can be designated by the operator with the operation part 16.

As stated above, even when displaying an MPR image, it is possible to grasp the relative positional relationship between the MPR image and the surface of the subject's body by displaying the surface site on the display 15.

(Wire Frame)

Figure 9:
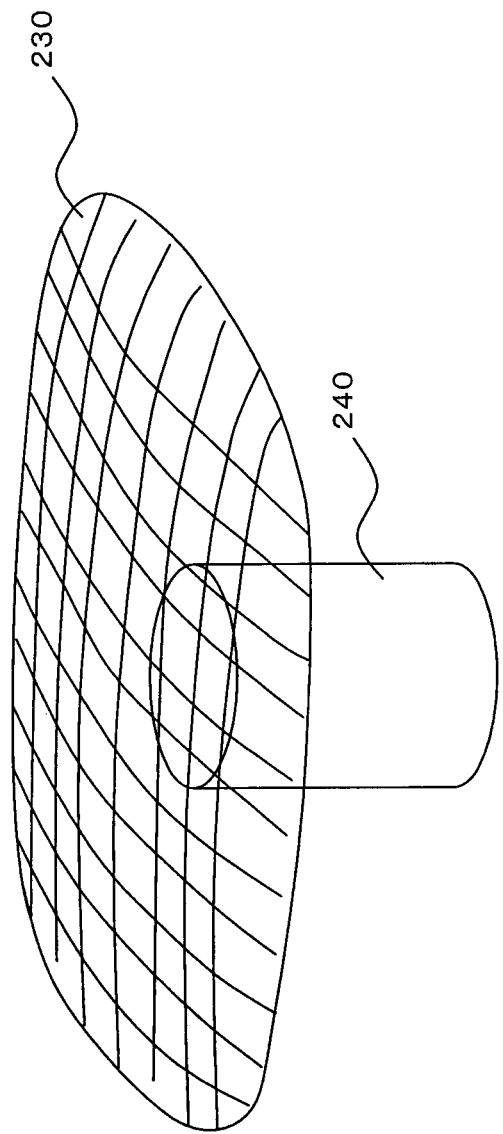
FIG. 9 is a schematic view for describing a surface site in volume data.

Moreover, the display controller 13 may control the display 15 to display a surface image showing a surface site in the form of a wire frame. A surface image in the form of a wire frame will be described with reference to FIG. 9. FIG. 9 is a schematic view for describing a surface site in volume data.

Upon reception of surface image data from the image generator 12, the display controller 13 controls the display 15 to display a surface site represented in the surface image data with net-like lines. For example, as shown in FIG. 9, the display controller 13 controls the display 15 to display a 3-dimensional image 240 showing an imaging site, and further controls the display 15 to display a surface site 230 in the form of a wire frame.

By thus displaying the surface image with a wire frame, the operator can observe a 3-dimensional image 240 of the imaging site from the side of the surface site. Consequently, it is possible to observe the internal site from the surface of the subject' body. For example, by displaying a 3-dimensional image of blood vessels and a surface image in the form of a wire frame, it is possible to check the position of the blood vessels from the side of the surface of the subject' body before an operation or at the time of puncture.

Moreover, the image generator 12 may generate different surface image data along a view direction different from those of the 3-dimensional image and the surface image based on the synthesized volume data. As described above, the image generator 12 generates 3-dimensional image data and surface image data along a view direction designated by the operator based on the synthesized volume data. In addition, the image generator 12 generates different surface image data along a different view direction based on the synthesized volume data. For example, the image generator 12 generates different surface image data, assuming the transmission/reception direction of the ultrasonic waves (depth direction) is a view direction. The display controller 13 then controls the display 15 to display the 3-dimensional image and surface image and further controls the display 15 to display a different surface image.

For example, as shown in FIG. 8, the display controller 13 controls the display 15 to display a 3-dimensional image 200 of an imaging site and a surface image 210, and further controls the display 15 to display a surface image 220 generated from a different view direction. For example, by setting the depth direction as the view direction, the surface of a subject viewed from above is shown in the surface image 220. The display controller 13 may reduce the display size of the surface image 220 to display the surface image 220 at a lower position on the screen of the display 15.

The surface image 220 shows a region scanned with ultrasonic waves. In other words, the surface image 220 shows the track of movement of the ultrasonic probe 2 on the surface of the subject. In this surface image 220, an area having been scanned and an area having not been scanned are shown distinctly. Thus, the operator can easily grasp the area having not been scanned. It is thereby possible to prevent an examination omission and to more accurately grasp a site for examination in a reexamination.

New volume data is generated by scanning while moving the ultrasonic probe on the surface of the subject's body. Every time new volume data is generated, the image generator 12 generates image data showing the new 3-dimensional image 200, image data showing the new surface image 210, and image data showing the new surface image 220. The display controller 13 updates the 3-dimensional image 200, the surface image 210 and the surface image 220 to new images, respectively, and controls the display 15 to display them.

Since the surface image 210 and the surface image 220 are thus updated in real time, it is possible to grasp a place having been scanned and a place having not been scanned, even during scan.

The user interface (UI) 14 is provided with the display 15 and the operation part 16. The display 15 is composed of a monitor such as a CRT and a liquid crystal display, on which a 3-dimensional image, a surface image, etc. are displayed. The operation part 16 is composed of a keyboard, a mouse, a trackball, a TCS (Touch Command Screen), etc., and is given various instructions through the operation by the operator.

The ultrasonic imaging apparatus 1 is provided with a controller, which is not shown. This controller is connected to each part of the ultrasonic imaging apparatus 1, and controls the operation of each part. For example, the controller controls the transmission and reception of ultrasonic waves by the transceiver 3.

Moreover, the image processor 5 is provided with a CPU (Central Processing Unit) not shown in the drawings and a storage device such as a ROM (Read Only Memory), a RAM (Random Access Memory) and an HDD (Hard Disk Drive) not shown in the drawings.

The storage device stores image-processing programs for executing the functions of the respective parts of the image processor 5. The image-processing programs include a reconstruction program for executing the function of the reconstructing part 6, a surface-site specifying program for executing the function of the surface-site specifying part 7, a synthesizing program for executing the function of the synthesizer 8, and an image-generating program for executing the function of the image generator 12. Moreover, the synthesizing program includes a matching program for executing the function of the matching part 9, and a coupling program for executing the function of the coupler 10. By the CPU executing the reconstruction program, volume data is reconstructed based on data in each cross-section. By the CPU executing the surface-site specifying program, a surface site in the volume data is specified. By the CPU executing the matching program, positions matching of imaging sites represented in a plurality of volume data is executed. By the CPU executing the coupling program, the plurality of volume data after position matching are coupled, and new synthesized volume data is generated. Then, by the CPU executing the image-generating program, 3-dimensional image data and surface image data are generated based on the volume data. The image-data storage 11 is composed of a storage device such as an HDD.

Moreover, the display controller 13 is provided with a CPU (not shown) and a storage device such as a ROM, a RAM and an HDD (not show). The storage device stores a display-controlling program for executing the function of the display controller 13. By the CPU executing the display-controlling program, a 3-dimensional image and a surface image are simultaneously displayed on the display 15.

(Ultrasonic Image Processing Apparatus)

An ultrasonic image processing apparatus may comprise the image processor 5, the display controller 13 and the user interface (UI) 14 that are described above. This ultrasonic image processing apparatus receives a plurality of volume data from an external ultrasonic imaging apparatus. The ultrasonic image processing apparatus specifies a surface site in each of the volume data, and couples the plurality of volume data. Furthermore, this ultrasonic image processing apparatus may be provided with a storage device that stores volume data acquired by the ultrasonic imaging apparatus.

For example, the ultrasonic imaging apparatus acquires a plurality of volume data at different positions on the surface of a subject. The ultrasonic image processing apparatus receives the plurality of volume data acquired by the ultrasonic imaging apparatus, and stores the plurality of volume data into the storage device. The surface-site specifying part 7 of the ultrasonic image processing apparatus specifies a surface site in each of the volume data. The synthesizer 8 generates synthesized volume data by synthesizing the plurality of volume data. The image generator 12 generates 3-dimensional image data that 3-dimensionally shows the morphology of the subject and surface image data showing the surface site based on the synthesized volume data. The display controller 13 controls the display 15 to simultaneously display a 3-dimensional image and a surface image.

As stated above, with the ultrasonic image processing apparatus, it is also possible to grasp the relative positional relationship between the 3-dimensional image and the surface of the subject, similarly in the abovementioned ultrasonic imaging apparatus 1.

(Operation)

Figure 10:
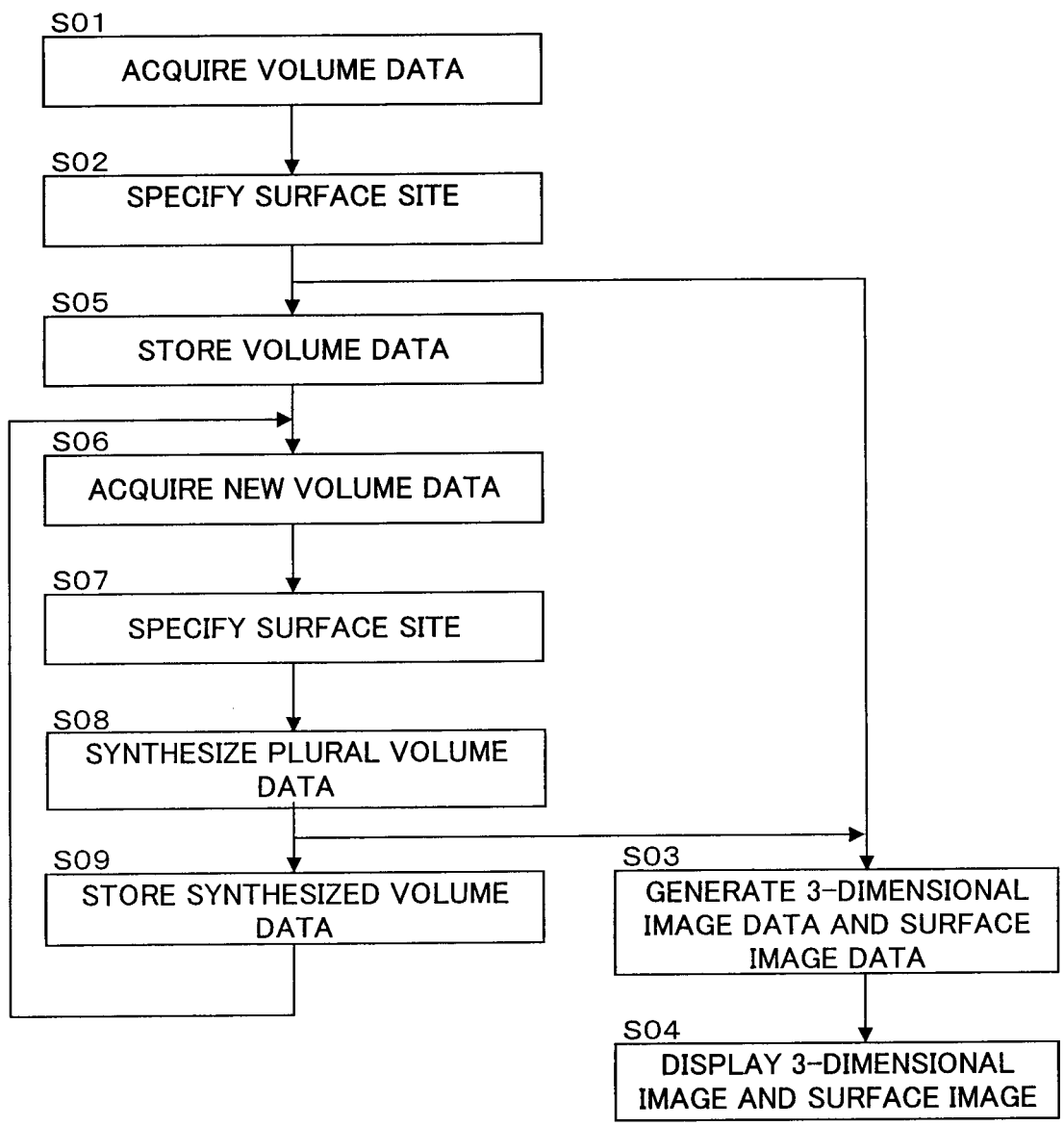
FIG. 10 is a flow chart showing a series of operations of an ultrasonic imaging apparatus according to an embodiment according to the present invention.

Next, an operation of the ultrasonic imaging apparatus in the embodiment of the present invention will be described with reference to FIG. 10. FIG. 10 is a flow chart for describing a series of operations by the ultrasonic imaging apparatus according to the embodiment of the present invention.

(Step S01)

First, with the ultrasonic probe 2 being applied to a subject, the subject is scanned with ultrasonic waves by using the ultrasonic probe 2 and the transceiver 3. Volume data showing a 3-dimensional region is acquired via this scanning. For example, the reconstructing part 6 reconstructs volume data based on ultrasonic raster data acquired by scan with ultrasonic waves.

(Step S02)

The surface-site specifying part 7 specifies a face corresponding to the surface of the subject's body in the generated volume data, and specifies a surface site included in the face. For example, as shown in FIG. 2, the surface-site specifying part 7 defines the face 21 at the shallowest position in the depth direction as a face corresponding to the surface of the subject in the volume data 20. The surface-site specifying part 7 then specifies surface site 22 within the face 21. For example, the surface-site specifying part 7 obtains the center position of the face 21 and specifies the surface site 22 having a specific range at the center position. The surface-site specifying part 7 outputs coordinate information of the surface site 22 to the image generator 12.

(Step S03)

The image generator 12 then sets a view direction for the volume data 20 and executes volume rendering on the volume data 20 along the view direction. Consequently, the image generator 12 thereby generates 3-dimensional image data that 3-dimensionally shows the imaging site 100 and surface image data showing the surface site 22. The image generator 12 generates the 3-dimensional image data and the surface image data in the same view direction, by executing volume rendering on the volume data 20 in the same view direction.

(Step S04)

The display controller 13 controls the display 15 to simultaneously display a 3-dimensional image that 3-dimensionally shows the imaging site 100 and a surface image showing surface site 22.

(Step S05)

Moreover, the image-data storage 11 stores coordinate information of the surface site 22 and the volume data 20 with the coordinate information of the surface site 22 incidental to the volume data 20.

(Step S06)

In addition, new volume data is acquired by scanning while moving the ultrasonic probe 2 on the surface of the subject.

(Step S07)

When volume data is newly acquired, the surface-site specifying part 7 specifies a surface site in the new volume data. The surface-site specifying part 7 then outputs coordinate information of the surface site in the new volume data to the synthesizer 8. For example, as shown in FIG. 4, when new volume data 30 is generated, the surface-site specifying part 7 specifies the surface site 31 in the new volume data 30. The surface-site specifying part 7 then outputs coordinate information of the surface site 31 in the new volume data 30 to the synthesizer 8.

(Step S08)

The synthesizer 8 reads out the volume data stored in the image-data storage 11 and synthesizes the newly generated volume data and the read-out volume data, thereby generating synthesized volume data. In the example shown in FIG. 4, the matching part 9 of the synthesizer 8 matches the morphology of the imaging site 100 shown in volume data 20 and the morphology of the imaging site 101 shown in volume data 30, thereby matching positions on the subject shown in the volume data 20 and the volume data 30. The coupler 10 of the synthesizer 8 then generates the synthesized volume data 40 shown in FIG. 5 by coupling volume data 20 and volume data 30 whose positions have been matched. Moreover, the coupler 10 generates data showing the new surface site 41 by interpolating data between surface site 22 and surface site 23. The synthesizer 8 then outputs the synthesized volume data 40 and coordinate information of surface site 41 to the image generator 12.

(Steps S03 and S04)

The image generator 12 then sets a view direction for the synthesized volume data 40 and executes volume rendering on the synthesized volume data 40 along the view direction. The image generator 12 thereby generates 3-dimensional image data that 3-dimensionally shows the imaging site 102 and surface image data showing surface site 41 (Step S03). The display controller 13 controls the display 15 to simultaneously display a 3-dimensional image that 3-dimensionally shows the imaging site 102 and a surface image showing surface site 41, instead of the previously displayed 3-dimensional image and surface image (Step S04). As described above, the display controller 13 updates the 3-dimensional image and surface image and controls the display 15 to display them.

(Step S09)

Moreover, the image-data storage 11 stores the coordinate information of the surface site 41 and the volume data 40 in a state where the coordinate information of surface site 41 is incidental to the volume data 40.

Different volume data is then newly acquired by scanning while moving the ultrasonic probe 2 on the surface of the subject's body. The process of Step S06 to Step S09 and the process of Steps S03 and S04 are then repeated. The 3-dimensional image and surface image are thereby updated and displayed on the display 15 every time new volume data is generated.

For example, by scanning while moving the ultrasonic probe 2 on the surface of the subject, new volume data 50 is generated as shown in FIG. 6 (Step S06). The surface-site specifying part 7 then specifies a surface site 51 in the new volume data 50 and outputs coordinate information of the surface site 51 to the synthesizer 8 (Step S07). The synthesizer 8 then reads out the synthesized volume data 40 stored in the image-data storage 11 and generates the new synthesized volume data 60 as shown in FIG. 7 by synthesizing the newly generated volume data 50 and the synthesized volume data 40 (Step S08). Moreover, the synthesizer 8 generates data showing the new surface site 61 by interpolating data between the surface site 41 and the surface site 51. The image generator 12 then generates 3-dimensional image data that 3-dimensionally shows the imaging site 104 and the surface image data showing surface site 61 by volume rendering of the synthesized volume data (Step S03). The display controller 13 updates the 3-dimensional image and the surface image, and controls the display 15 to simultaneously display the 3-dimensional image showing the imaging site 104 and the surface image showing surface site 61 (Step S04).

As stated above, by simultaneously displaying the 3-dimensional image of the subject and the surface image of the surface site on the display 15, it is possible to easily grasp the relative positional relationship between the 3-dimensional image and the surface of the subject. Consequently, it is possible to easily grasp a part having been scanned. Moreover, by updating the 3-dimensional image and the surface image and displaying the new 3-dimensional image and surface image every time new volume data is generated, it is possible to track the positional relationship between the 3-dimensional image and the surface of the subject in real time.

What is claimed is:

1. An ultrasonic imaging apparatus, comprising:
   an imaging part, including a transceiver and a signal processor, the imaging part configured to cause an ultrasonic probe having a plurality of transducers to transmit ultrasonic waves to a subject, and receive reflected waves from the subject to acquire a plurality of volume data of the subject;
   an image processor configured to execute one or more programs that cause the image processor to
      specify a surface of the subject, the surface corresponding to a contact surface between the ultrasonic probe and the subject, and to specify a surface site included in the specified surface of the subject, for each of the plurality of volume data;
      execute position matching of an imaging site inside the subject indicated by the plurality of volume data, combine the plurality of volume data after position matching, and combine the surface sites specified in the respective volume data so as to generate synthesized volume data;
      generate, using the synthesized volume data, morphology image data showing a three-dimensional morphology of the imaging site inside the subject, and generate, using the synthesized volume data, surface image data showing the combined surface sites; and
   a display controller configured to control a display to display a morphology image based on the morphology image data, and display a surface image based on the surface image data, the surface image illustrating the combined surface sites of the subject scanned by the imaging part.

2. The ultrasonic imaging apparatus according to claim 1, wherein the image processor is further configured to specify, in each of the plurality of volume data, a nearest position to a transmission/reception side of the ultrasonic waves, define a face substantially orthogonal to the transmission/reception side at the nearest position as the surface of the subject, and specify the surface site within the defined face.

3. The ultrasonic imaging apparatus according to claim 1, wherein the image processor is further configured to specify, in each of the plurality of volume data, a nearest place based on a strength of the reflected waves along a transmission/reception direction of the ultrasonic waves, define a face including the specified nearest place and being substantially orthogonal to the transmission/reception direction, as a face corresponding to the surface of the subject, and specify the surface site within the defined face.

4. The ultrasonic imaging apparatus according to claim 1, wherein the image processor is further configured to determine, in a face corresponding to the surface of the subject, the surface site based on a strength of the reflected waves.

5. The ultrasonic imaging apparatus according to claim 1, wherein the image processor is further configured to interpolate between the surface sites specified in the respective volume data and combine the surface sites.

6. The ultrasonic imaging apparatus according to claim 1, wherein
the image processor is further configured to extract data showing a desired region from the synthesized volume data, and generate the morphology image data showing a morphology of the desired region based on the extracted data; and
the display controller is configured to control the display to display the morphology image based on the morphology image data of the desired region and the surface image based on the surface image data.

7. The ultrasonic imaging apparatus according to claim 1, wherein
the image processor is further configured to generate the morphology image data and the surface image data of a same view direction based on the synthesized volume data; and
the display controller is configured to control the display to display the morphology image and the surface image of the same view direction.

8. The ultrasonic imaging apparatus according to claim 1, wherein
the image processor is further configured to generate the morphology image data and the surface image data, and generate different surface image data along a view direction different from the surface image data; and
the display controller is configured to control the display to display the morphology image and the surface image, and control the display to display a different surface image based on the different surface image data.

9. The ultrasonic imaging apparatus according to claim 1, wherein
the image processor is further configured to generate 3-dimensional image data that 3-dimensionally shows the morphology of the subject as the morphology image data based on the synthesized volume data; and
the display controller is configured to control the display to display a 3-dimensional image based on the 3-dimensional image data, and the surface image.

10. The ultrasonic imaging apparatus according to claim 1, wherein the image processor is further configured to execute the position matching by executing pattern matching of the morphology of the subject shown in each of the plurality of volume data, and generate the synthesized volume data.

11. The ultrasonic imaging apparatus according to claim 1, further comprising:
a position detector configured to detect a position on the subject where the volume data has been acquired, wherein:
the image processor is further configured to execute position matching based on the position on the subject of each of the volume data detected by the position detector, and generate the synthesized volume data.

12. The ultrasonic imaging apparatus according to claim 1, wherein
the image processor is configured to specify the surface site as a region, for each of the plurality of volume data;
the image processor is configured to combine the plurality of volume data after position matching, and combine the surface sites as the regions specified in the respective volume data, so as to generate the synthesized volume data; and
the image processor is configured to generate the morphology image data and the surface image data showing the combined surface sites as regions, by processing the synthesized volume data.

13. A method for generating an ultrasonic image, comprising:
transmitting ultrasonic waves from an ultrasonic probe having a plurality of transducers to a subject, and receiving reflected waves from the subject to acquire a plurality of volume data of the subject;
specifying a surface of the subject, the surface corresponding to a contact surface between the ultrasonic probe and the subject, and specifying a surface site included in the specified surface of the subject, for each of the plurality of volume data;
executing position matching of an imaging site in the subject indicated by the plurality of volume data, combining the plurality of volume data after the position matching, and combining the surface sites specified in the respective volume data so as to generate synthesized volume data;
generating, using the synthesized volume data, morphology image data showing a three-dimensional morphology of the imaging site inside the subject, and generating, using the synthesized volume data, surface image data showing the combined surface sites; and
displaying a morphology image based on the morphology image data and a surface image based on the surface image data, the surface image illustrating the combined surface sites of the subject scanned by the ultrasonic probe.

14. The method for generating an ultrasonic image according to claim 13, wherein
the specifying step further comprises specifying, in each of the plurality of volume data, a nearest position to a transmission/reception side of the ultrasonic waves, defining a face substantially orthogonal to the transmission/reception side at the nearest position as the surface of the subject, and specifying the surface site within the defined face.

15. The method for generating an ultrasonic image according to claim 13, wherein the specifying step further comprises specifying, in each of the plurality of volume data, a nearest place based on a strength of the reflected waves along a transmission/reception direction of the ultrasonic waves, defining a face including the specified nearest place and substantially orthogonal to the transmission/reception direction as a face corresponding to the surface of the subject, and specifying the surface site within the defined face.

16. The method for generating an ultrasonic image according to claim 13, wherein the specifying step further comprises determining, in the face corresponding to the surface of the subject, the surface site based on a strength of the reflected waves.

17. The method for generating an ultrasonic image according to claim 13, wherein the executing step further comprises combining the surface sites by interpolating between the surface sites specified in the respective volume data.

18. The method for generating an ultrasonic image according to claim 13, wherein
data showing a desired region is extracted from the synthesized volume data, and the morphology image data showing a morphology of the desired region is generated based on the extracted data; and the morphology image based on the morphology image data of the desired region and the surface image based on the surface image data are displayed.

19. An ultrasonic imaging apparatus, comprising:

an imaging part, including a transceiver and a signal processor, the imaging part being configured to cause an ultrasonic probe having a plurality of transducers to transmit ultrasonic waves to a subject through media, and receive reflected waves from the subject through the media, to acquire a plurality of volume data of the subject;

an image processor configured to execute one or more programs that cause the image processor to specify a surface of the subject, the surface corresponding to a contact surface between the media and the subject, and to specify a surface site included in the specified surface of the subject, for each of the plurality of volume data;

execute position matching of an imaging site inside the subject indicated by the plurality of volume data, combine the plurality of volume data after position matching, and combine the surface sites specified in the respective volume data, so as to generate synthesized volume data;

generate, using the synthesized volume data, morphology image data showing a three-dimensional morphology of the imaging site inside the subject, and generate, using the synthesized volume data, surface image data showing the combined surface sites; and a display controller configured to control a display to display a morphology image based on the morphology image data, and display a surface image based on the surface image data, the surface image illustrating the combined surface sites of the subject scanned by the imaging part.

20. The ultrasonic imaging apparatus according to claim 19, wherein the image processor is configured to specify the surface site as a region, for each of the plurality of volume data;

the image processor is configured to combine the plurality of volume data after position matching, and combine the surface sites as the regions specified in the respective volume data, so as to generate the synthesized volume data; and the image processor is configured to generate the morphology image data and the surface image data showing the combined surface sites as regions, by processing the synthesized volume data.

21. The ultrasonic imaging apparatus of claim 19, wherein the image processor is further configured to specify, in each of the plurality of volume data, a nearest position to a transmission/reception side of the ultrasonic waves, define a face substantially orthogonal to the transmission/reception side at the nearest position as the surface of the subject, and specify the surface site within the defined face.

\* \* \* \* \*